(12) United States Patent
Mathew

(10) Patent No.: US 8,784,314 B2
(45) Date of Patent: Jul. 22, 2014

(54) BIOMETRICALLY ENABLED IMAGING SYSTEM

(75) Inventor: Prakash Parayil Mathew, Mukwonago, WI (US)

(73) Assignee: GE Medical Sytems Global Technology Company LLC, Waukesha, WI (US)

(*) Notice: Subject to any disclaimer, the term of this patent is extended or adjusted under 35 U.S.C. 154(b) by 2939 days.

(21) Appl. No.: 10/681,634

(22) Filed: Oct. 8, 2003

(65) Prior Publication Data

US 2005/0080326 A1  Apr. 14, 2005

(51) Int. Cl.
*A61B 8/00* (2006.01)

(52) U.S. Cl.
USPC .......................................................... 600/437

(58) Field of Classification Search
CPC .... A61B 8/467; G06F 21/32; G06K 9/00382; G06Q 20/4014; G06Q 20/40145; G06Q 50/22; H04L 2209/88; H04L 63/0861; H04L 9/3231
USPC ............ 600/407–410, 300, 437; 378/197, 92; 382/115; 713/186
See application file for complete search history.

(56) References Cited

U.S. PATENT DOCUMENTS

| | | | | |
|---|---|---|---|---|
| 5,315,999 A | * | 5/1994 | Kinicki et al. | 600/443 |
| 5,544,654 A | * | 8/1996 | Murphy et al. | 600/443 |
| 5,930,804 A | * | 7/1999 | Yu et al. | 707/104.1 |
| 6,129,671 A | * | 10/2000 | Hastings | 600/437 |
| 6,233,476 B1 | * | 5/2001 | Strommer et al. | 600/424 |
| 6,260,021 B1 | * | 7/2001 | Wong et al. | 705/2 |
| 6,411,836 B1 | * | 6/2002 | Patel et al. | 600/407 |
| 6,475,146 B1 | * | 11/2002 | Frelburger et al. | 600/437 |
| 6,506,155 B2 | * | 1/2003 | Sluis | 600/437 |
| 6,587,830 B2 | * | 7/2003 | Singer | 705/3 |
| 6,618,806 B1 | * | 9/2003 | Brown et al. | 713/186 |
| 6,656,119 B2 | * | 12/2003 | Sasaki et al. | 600/437 |
| 6,674,537 B2 | | 1/2004 | Kadowaki | |
| 6,837,422 B1 | * | 1/2005 | Meder | 235/375 |
| 6,837,853 B2 | * | 1/2005 | Marian | 600/437 |
| 7,904,824 B2 | * | 3/2011 | Stern et al. | 715/771 |
| 2002/0174344 A1 | * | 11/2002 | Ting | 713/185 |
| 2003/0088781 A1 | * | 5/2003 | ShamRao | 713/186 |

(Continued)

FOREIGN PATENT DOCUMENTS

EP  1209611 A1   5/2002
EP  0886428 B1  10/2004

(Continued)

OTHER PUBLICATIONS

Japanese Application No. 2004-294834 Preliminary Rejection (4 pages) (Jul. 13, 2010).
Japanese Application No. 2004-294834 Office Action (5 pages) (Dec. 22, 2011).

*Primary Examiner* — Elmer Chao
(74) *Attorney, Agent, or Firm* — McAndrews, Held & Malloy, Ltd.; Jacob Groethe; David Bates

(57) ABSTRACT

A medical imaging system including a central processing unit, a data storage unit in communication with said central processing unit, an imaging device in electrical communication with the central processing unit, and a biometric authorization unit in electrical communication with the central processing unit. A user inputs a biometric identifier into the biometric authorization unit in order to enable the medical imaging system.

11 Claims, 7 Drawing Sheets

(56) References Cited

U.S. PATENT DOCUMENTS

| | | |
|---|---|---|
| 2003/0097054 A1 | 5/2003 | Sasaki et al. |
| 2003/0140928 A1 | 7/2003 | Bui et al. |
| 2003/0187689 A1 | 10/2003 | Barnes et al. |
| 2003/0200217 A1* | 10/2003 | Ackerman ................. 707/9 |
| 2004/0249673 A1* | 12/2004 | Smith ....................... 705/2 |
| 2005/0054926 A1* | 3/2005 | Lincoln ................... 600/443 |

FOREIGN PATENT DOCUMENTS

| | | |
|---|---|---|
| JP | 11-017862 | 1/1999 |
| JP | 2002-236750 A | 8/2002 |
| JP | 2003-058204 A | 2/2003 |

* cited by examiner

BIOMETRICALLY ENABLED IMAGING SYSTEM

BACKGROUND OF THE INVENTION

Embodiments of the present invention generally relate to imaging systems, such as medical imaging systems, and more particularly to a system and method of identifying operators of an imaging system through biometric identifiers.

Various medical imaging systems and modalities are known and used for diagnosis and assisting in treatment and surgery. For example, ultrasound, magnetic resonance (MR), computed tomography, and other types of imaging modalities have been used to image various anatomical features. Ultrasound imaging systems represent a useful and versatile imaging modality. Typically, ultrasound imaging systems are easy to use, cost-efficient, portable, and do not subject a patient to harmful ionizing radiation.

Ultrasound imaging system operators, i.e., sonographers, are typically trained technicians whose skills are important in achieving accurate, high-quality images. During a typical ultrasound imaging session, a sonographer manipulates an ultrasound probe over a portion of a patient's anatomy proximate a region of interest to be imaged. Each sonographer may have particular preferences with respect to various imaging parameters and probe characteristics. For example, a sonographer may prefer a particular image brightness, configuration, or ultrasound probe set-up (for example, orientation of an imaging element on the ultrasound probe). Typically, before each imaging session, the sonographer adjusts the ultrasound imaging system to suit his/her particular preferences. The process of adjusting the system to an individual's particular preferences takes time. Further, each time a different individual uses the system, different adjustments are made that conform to that individual's preferences.

Further, with increased security and privacy requirements, only certain medical practitioners may be authorized to use a particular imaging system. However, many imaging systems do not include features that prevent unauthorized users from using the systems. Some systems require the use of a password (including words and PIN numbers) and/or a key or swipe card in order for imaging to commence. However, passwords may be intercepted, and keys, swipe cards and the like may fall into the hands of unauthorized users.

Thus, a need exists for a more secure system and method of medical imaging. A need exists for a system and method in which only authorized users may use medical imaging systems. Further, a need exists for a more efficient system and method of imaging a patient.

SUMMARY OF THE INVENTION

Certain embodiments of the present invention provide a medical imaging system including a central processing unit, a data storage unit in electrical communication with the central processing unit, an imaging device in electrical communication with the central processing unit, and a biometric authorization unit in electrical communication with the central processing unit. A user inputs a biometric identifier, such as a fingerprint, handprint, iris, retina, facial thermogram, voice, or the like, into the biometric authorization unit in order to enable use of the medical imaging system. Biometric data extracted from the biometric identifier is compared with stored biometric data in the data storage unit. The stored biometric data may be associated with personal identification information, including an individual operator's name, occupation, address, or other such information. Additionally, user preference information, such as monitor viewing and instrument imaging preferences, may also be associated with the stored biometric data and with the personal identification information.

In general, use of the imaging system is allowed when a match exists between the biometric data extracted from the biometric identifier and the stored biometric data. Information regarding the use of the medical imaging system by the user is stored in the data storage unit. For example, information regarding the number of times an individual has used the imaging system, times when the individual used the imaging system, and length of imaging sessions may be stored in the data storage unit. Further, the results of the imaging session, i.e., resulting images, may be stored in the data storage unit and associated with the individual who captured the images through the imaging system.

The imaging device may be an ultrasound probe used within an ultrasound imaging system. Alternatively, the imaging system may be a Computed Tomography (CT), X-ray (either film-based or digital), Positron Emission Tomography (PET), Single Photon Emission Computed Tomography (SPECT), Electron Beam Tomography (EBT), Magnetic Resonance (MR), or an image-guided surgery system.

Certain embodiments of the present invention also provide a medical imaging network including a plurality of medical imaging systems in communication with one another. The network may also include a central management station in communication with each of the medical imaging systems. Biometric data extracted from a biometric identifier and system use information may be stored in a central data storage unit in the central management station and/or within individual data storage units in the individual imaging systems.

Certain embodiments of the present invention also provide a method of using a medical imaging system including registering to use the medical imaging system, storing biometric data and associated personal information, and enabling use of the medical imaging when biometric data input at a biometric authorization unit matches stored biometric data. The registering step includes inputting a biometric identifier into a biometric authorization unit, inputting personal information into the medical imaging system, and associating biometric data extracted from the biometric identifier with the personal information. The method may also include restricting access to the registering step by inputting a password.

Certain embodiments of the present invention also provide a method of using audio/video equipment including registering to use the audio/video equipment by inputting biometric data, storing the biometric data, and enabling use of the audio/video equipment when biometric data input after the registration matches the stored biometric data. The audio/video equipment may be any one of a television, camera, CD player, DVD player, or car stereo. Access to registration may be restricted through requiring the submission of a password. That is, a person may register if he/she first provides a password or PIN number.

Figure 1:
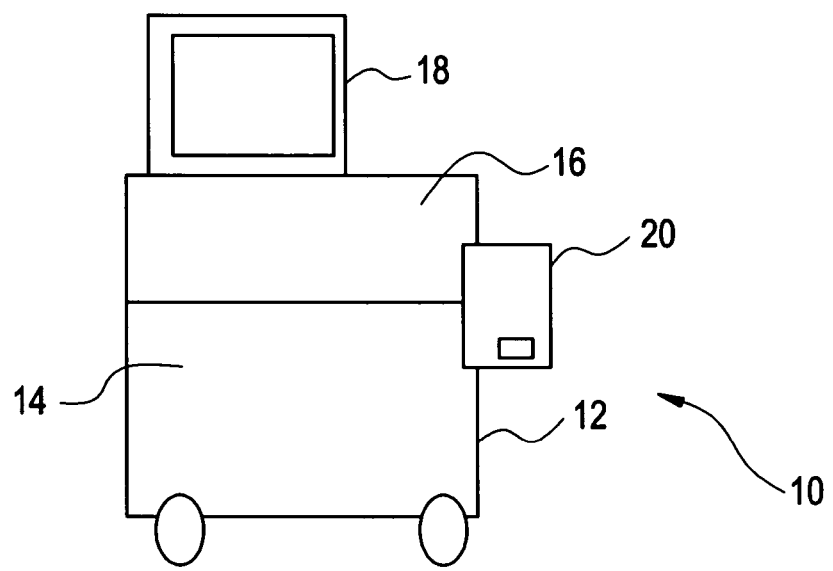
FIG. 1 illustrates an imaging system according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates a medical imaging system 10 according to an embodiment of the present invention. The imaging system 10 includes a main body 12 housing a central processing unit 14, electronics, and other components, a user control input unit 16 (such as a keyboard, mouse, or touchscreen monitor), an imaging device (such as an ultrasound probe), a display unit 18, and an authorization unit 20. The user control input unit 16, the imaging equipment, the display unit 18 and the authorization unit 20 are each in operative electrical communication with the central processing unit 14.

The imaging system 10 may be an ultrasound system, or it may be various other types of imaging systems, such as a fluoroscopic, MR, CT imaging system. For example, the imaging system may include an X-ray C-arm having an X-ray source positioned on one distal end of the arm, with a detector positioned on the other distal end of the arm, such as shown and described in U.S. Pat. No. 6,104,780, entitled "Mobile bi-planar fluoroscopic imaging apparatus," U.S. Pat. No. 5,802,719, entitled "One piece C-arm for x-ray diagnostic equipment," and U.S. Pat. No. 5,627,873, entitled "Mini C-arm assembly for mobile x-ray imaging system," all of which are hereby incorporated by reference in their entireties. Optionally, the imaging system may be an MR system, such as described in U.S. Pat. No. 6,462,544, entitled "Magnetic resonance imaging apparatus," which is also hereby incorporated by reference in its entirety.

The authorization unit 20 may be configured to identify fingerprints, faces, voices, or various other distinct characteristics of an individual. The authorization unit 20 is used to identify an operator of the imaging system 10. Biometric data input at the authorization unit 20 is compared with stored biometric data. The stored biometric data may be stored in a data storage unit, i.e., a memory, of the central processing unit 14, or it may be stored in a data storage unit of a central processing unit of a remote central management station that is in communication with the central processing unit 14 (such as through modems, DSL lines, T1 or T3 lines, wireless communication lines, and the like). If the biometric data input at the authorization unit does not match stored biometric data, access to the imaging system 10 is denied. If, however, the biometric data input at the authorization unit 20 matches stored biometric data, a person is allowed to use the imaging system. Further, stored user preferences correlated with the stored biometric data may then be applied to the imaging system 10 based on the input biometric data, as discussed in more detail below.

Figure 2:
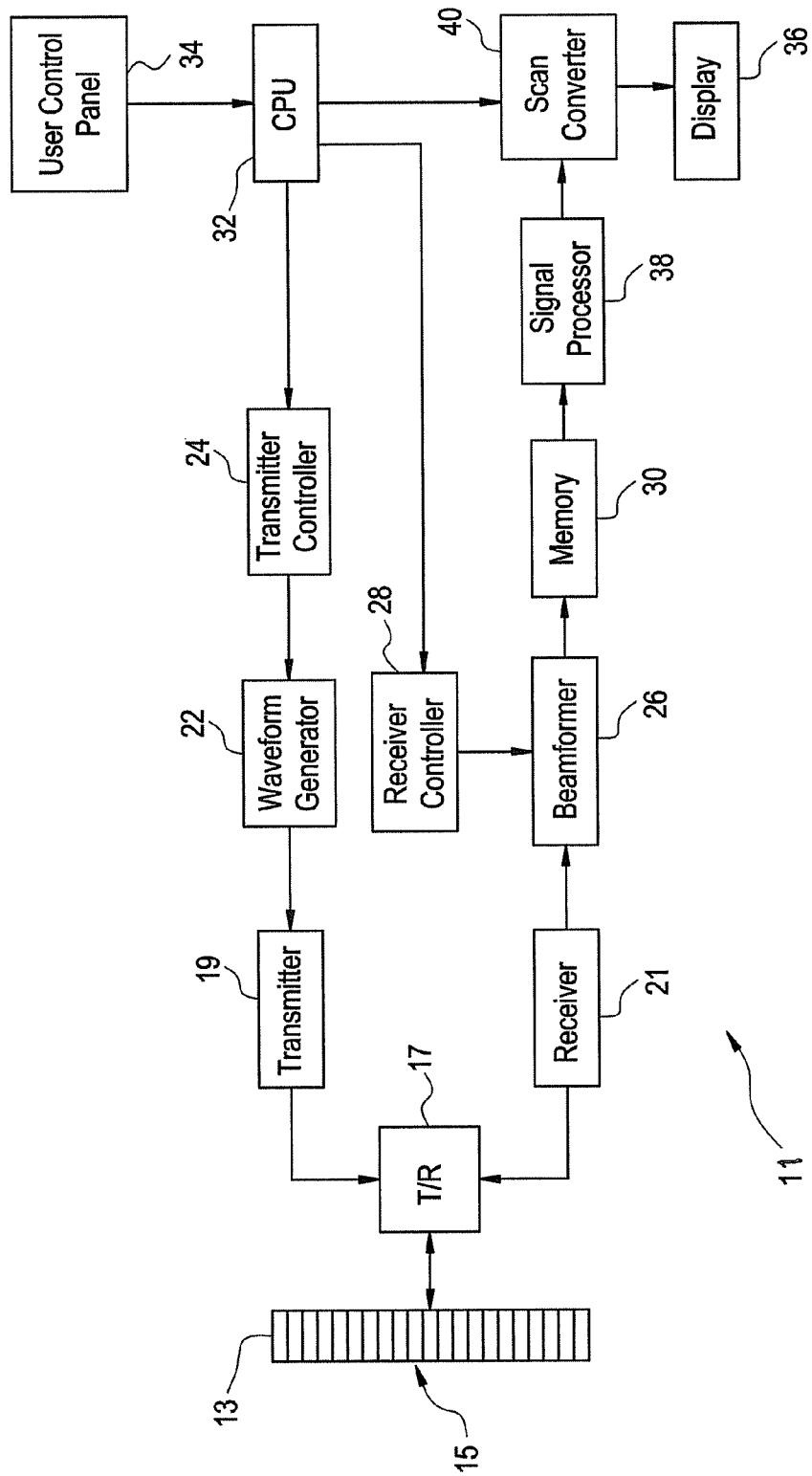
FIG. 2 illustrates a block diagram of an ultrasound diagnostic imaging system according to an embodiment of the present invention.

FIG. 2 illustrates a block diagram of an ultrasound diagnostic imaging system 11 according to an embodiment of the present invention. The system 11 includes a transducer array 13 contained within an ultrasonic probe 15. The transducer array 13 is coupled via a transmit/receive switch 17 to a transmitter 19 and a receiver 21. The transmitter 19 drives the transducer array 13 to fire pulses, or emit pulsed ultrasonic signals, into an object or body. A waveform generator 22 generates waveforms that may be transmitted sequentially in time, along the same spatial line, by the transmitter 19, which is controlled by transmitter controller 24.

The ultrasonic signals are backscattered from structures in the body, like blood cells, muscular tissue or contrast microbubbles, to produce echoes that are detected by the transducer array 13. The echoes from each transmit pulse are received sequentially by receiver 21. The received echoes are passed through a beamformer 26, which performs beamforming and filtering operations and is controlled by a receiver controller 28. The received signals are then stored in memory 30. A central processing unit 32 coordinates higher-level functions of the ultrasound imaging system, such as user inputs from a user control panel 34, display of data on a display 36, and the like. Received signals are processed and stored in the memory 30. A signal processor 38 filters and processes the signals. The resultant processed signals may be envelope detected and log compressed, then sent by the signal processor 38 to a scan converter 40. The processed signals are then displayed by the display 36.

Figure 3:
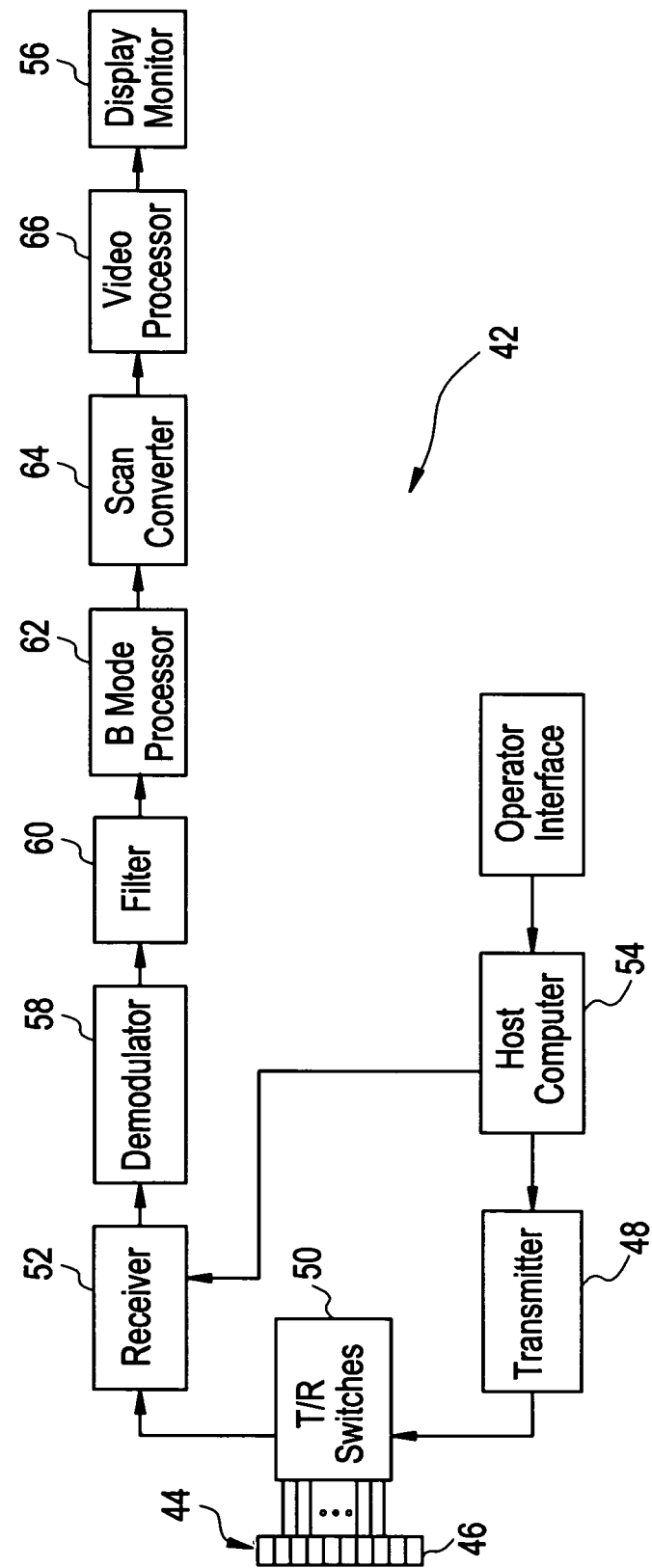
FIG. 3 illustrates a block diagram of an ultrasound diagnostic imaging system according to an embodiment of the present invention.

FIG. 3 illustrates a block diagram of an ultrasound diagnostic imaging system 42 according to an embodiment of the present invention. The system 42 includes a transducer array 44 including a plurality of separately driven transducer elements 46, each of which produces a burst of ultrasonic energy when energized by a pulsed waveform produced by a transmitter 48 and sent through a set of transmit/receive (T/R) switches 50 switched to a transmit state. The ultrasonic energy reflected back to the transducer array 44 from a patient's anatomy under study is converted to an electrical signal by each receiving transducer element 46 and applied separately to a receiver 52 through T/R switches 50, which have switched to a receive state. The T/R switches 50 may be diodes that protect the receive electronics from the high voltages generated by the transmit electronics. The transmit signal causes the diodes to shut off or limit the signal to the receiver 52. The transmitter 48 and the receiver 52 are operated under control of a host computer (i.e., a central processing unit) 54. A complete scan is performed by acquiring a series of echoes after the transmitter 48 has been gated ON momentarily to energize each transducer element 46 in the transmit aperture, and the subsequent echo signals in the form of low-level analog RF (radio frequency) signals produced by each transducer element 46 in response to reflected ultrasonic energy are applied to the receiver 52. The receiver 52 combines the separate echo signals from each transducer element 46 to produce a single echo signal that is used to produce a line in an image on a display monitor 56.

The receiver 52 is responsible for analog-to-digital conversion and for receive beamforming. In baseband imaging systems, the beamsummed signal is supplied to a demodulator 58, which converts the beamsummed signal into baseband in-phase I and quadrature Q receive components. The I and Q acoustic data vectors from the demodulator 58 are sent to respective FIR (finite impulse response) filters 60 that are programmed with filter coefficients to pass a band of frequencies preferably centered at the center frequency of the transmit waveform or at a harmonic or subharmonic frequency thereof.

Vectors of filtered I and Q acoustic data are sent to a B-mode processor 62, which converts the I and Q acoustic data into a log-compressed version of the signal envelope. The B-mode function images the time-varying amplitude of the envelope of the signal as a gray scale. The envelope of a baseband signal is the magnitude of the vector that I and Q represent.

The B-mode intensity data is provided to a scan converter 64 having a B-mode acoustic line memory followed by an X-Y display memory. The acoustic line memory accepts the processed vectors of B-mode intensity data and interpolates where necessary, and also performs a coordinate transformation of the B-mode intensity data from polar coordinate sector format or Cartesian coordinate linear format to appropriately scaled Cartesian coordinate display pixel intensity data, which are stored in the X-Y display memory.

The scan-converted frames are passed to a video processor 66, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are sent to display monitor 56 for display.

Embodiments of the present invention may be used with a variety of ultrasound imaging systems. For example, the ultrasound imaging system may be a two-dimensional, or three-dimensional ultrasound system. Also, the ultrasound systems may be, for example, B-mode, Doppler, or other types of systems known and used in the art. Further, various types of ultrasound probes may be used including probes having sector, linear, curved, or active matrix arrays. Overall, embodiments of the present invention may be used with any type of medical imaging system, including magnetic resonance (MR), computed tomography (CT), fluoroscopic, and the like. Additionally, embodiments of the present invention may also be used with non-medical imaging systems, such as television cameras, camcorders, thermo-imaging systems, light amplification viewing and imaging systems (e.g., night vision goggles), and the like.

Figure 4:
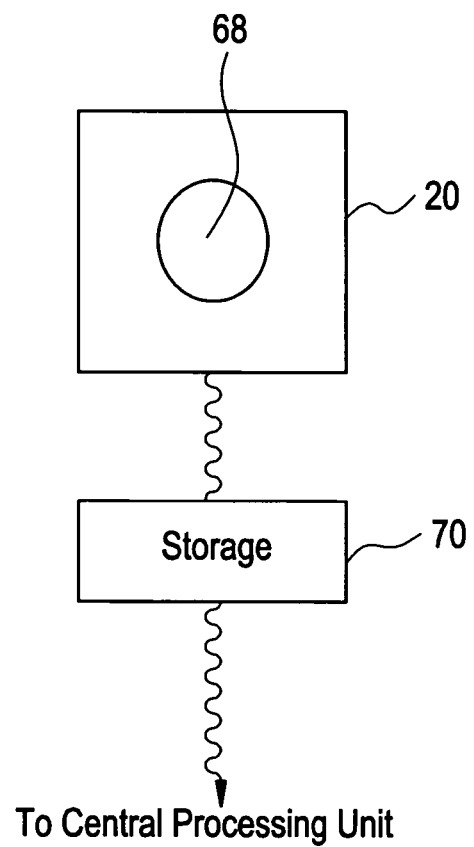
FIG. 4 illustrates a block diagram of an authorization unit according to an embodiment of the present invention.

FIG. 4 is a block diagram of the authorization unit 20 according to an embodiment of the present invention. In order to use the imaging system 10 (shown in FIG. 1), an individual first registers. The individual may register at a central management station that is networked into the imaging system 10 or at the imaging system 10 itself. The central management station also includes an authorization unit that may receive biometric data. Registration requires the individual to input biometric data into the authorization unit 20. The authorization unit 20 registers the individual's biometric identifier, such as a fingerprint, retina, face contour, or the like, via a biometric reader 68. The individual presents a biometric identifier to the biometric reader 68. The biometric reader 68 scans the individual's biometric identifier, such as a fingerprint, and captures various points of identification from the biometric identifier. The biometric reader 68 scans the biometric identifier and extracts biometric indicators from the biometric identifier. The biometric reader 68 subjects the biometric indicators to a recognition algorithm that converts the scanned biometric identifier image into a much smaller data code. The biometric reader 68 then sends the smaller data code of biometric identification, or biometric data, to a data storage unit 70 within the authorization unit 20. The data storage unit 70 may be included within the authorization unit 20, or it may be included within the central processing unit 14 of the imaging system 10.

Referring again to FIG. 1, the individual may input personal information such as name, address, occupation, security clearance information and the like, via the user control input unit 16. The control input unit 16 may be a computer keyboard, mouse, or touch-sensitive monitor. The personal information is then sent to the data storage unit 70. An encoder then receives the biometric data and the personal information from the data storage unit 70. The personal information and the biometric data may then be encoded. That is, the encoder may match and combine the personal information with the biometric data. The encoded personal information and biometric data are then stored within the central processing unit 14, or within a central processing unit of a central management station networked into the imaging system 10. Once the personal information and biometric data have been matched and combined, registration is complete.

Additionally, an individual may store associated user preferences with the personal information and biometric data. For example, a user may be prompted, by way of the display unit, to set imaging preferences. The individual may adjust brightness, color, contrast, display configuration (such as multiple views of various portions of an anatomy) and the like on the display unit 18. Also, the individual may adjust various parameters of the imaging equipment. For example, if an ultrasound imaging system is used, the individual may adjust the number of active transducer elements on the ultrasound probe, the intensity of ultrasound signals transmitted from the probe, default power levels, gain levels, depth, probe type, application type, mode type, imaging depth, position and number of focal zones, field of view, filter activation, spatial compounding, voice command presets, and the like.

Once the individual has set up the imaging system to his/her particular preferences, the individual may be prompted to save the settings. If the individual chooses to save the settings, the settings are then associated with that individual. That is, the individual's imaging preferences are matched and combined with his/her personal information and biometric data and stored in the data storage unit 70. Thus, when an individual enables the imaging system 10 at a later date by inputting his/her biometric data into the authorization unit 20, the imaging system 10 will automatically adjust to the individual's preferences. Because the imaging system 10 may be automatically adjusted to an individual's preferences in this way, less time is expended in setting the imaging system 10 to an individual's particular preferences.

Once an individual has registered, the individual may enable use of the imaging system 10. In order to use the imaging system 10, the individual presents a biometric identifier to the authorization unit 20. For example, if the authorization unit 20 is configured to accept fingerprints, the individual inputs a fingerprint onto the authorization unit 20. The biometric data scanned from the biometric identifier is compared with stored biometric data. If a match exists, the personal identification information associated with the stored biometric data allows the imaging system to discern the identity of the individual. The individual may then use the imaging system 10 to image a patient. Alternatively, only sets of biometric data may be stored (but not personal information), thereby permitting use of the imaging system 10 when biometric data matches stored biometric data.

If, when the individual presents a biometric identifier, a match between the biometric data presented at the authorization unit 20 and biometric data stored in the data storage unit 70 does not exist, the individual may be prompted to register. The registration process may include a password or other gate keeping protocol (such as the use of a key or swipe card) to prevent unauthorized users from registering. For example, the first step of registration may be to input a password provided to a user by a system administrator.

Figure 5:
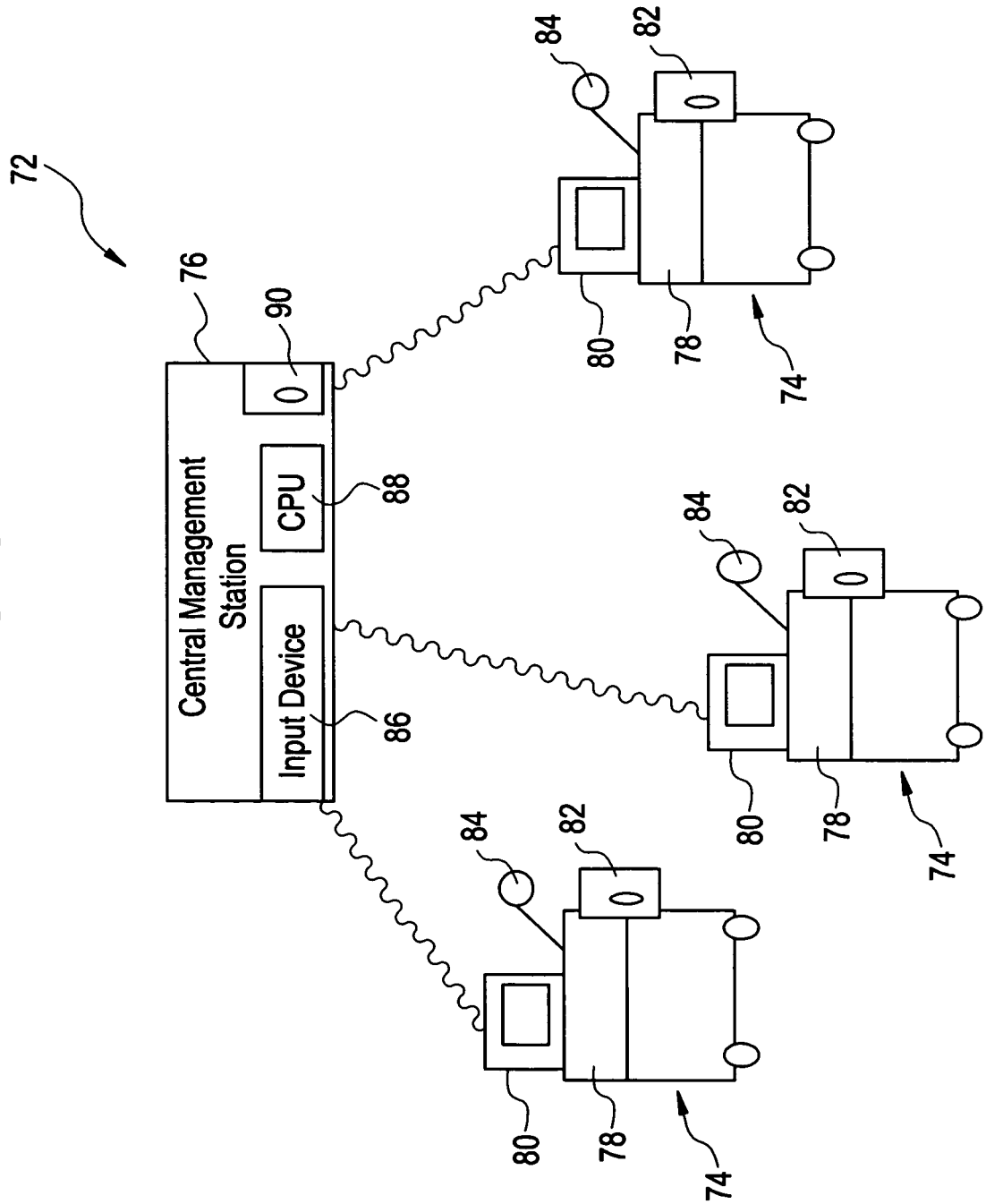
FIG. 5 illustrates a block diagram of an imaging system network according to an embodiment of the present invention.

FIG. 5 illustrates a block diagram of an imaging system network 72 according to an embodiment of the present invention. The network 72 includes a plurality of imaging systems 74, which may be ultrasound imaging systems, X-ray imaging systems, or various other types of modalities. Each imaging system 74 is networked into a central management station 76 through various types of internet connections (modem, wireless, DSL, T1, or the like). As discussed above, each imaging system 74 includes an input device 78 (e.g., a keyboard), a display unit 80, an authorization unit 82, and an imaging device 84 (such as an ultrasound probe), all of which are in operative electrical communication with a processing unit (not shown). The central management station 76 includes an input device 86 operatively connected to a central processing unit 88, which is also operatively connected to an authorization unit 90. Registration, as discussed above, may take place at any of the imaging systems 74, or at the central management station 76.

Biometric data and user preference data may be stored at either the central management station 76 or the imaging systems 74. Further, biometric data and user preference data may be periodically downloaded to the individual imaging systems 74 from the central management station 76. Also, biometric data and user preference data may be uploaded to the central management station 76 from the individual imaging systems 74.

Alternatively, each of the imaging systems 74 may be networked directly with each other, as opposed to being networked through the central management station 76. Further, the network 72 may not include the central management station 76, but instead include a plurality of imaging systems 74 networked with one another. Each imaging system 74 may be a different modality. For example, one imaging system 74 may be an ultrasound system, while another may be an X-ray C arm, while another may be an electromagnetic tracking system. Additionally, the authorization unit for each imaging system may be disabled through the use of a password, swipe card, key, or the like.

Figure 6:
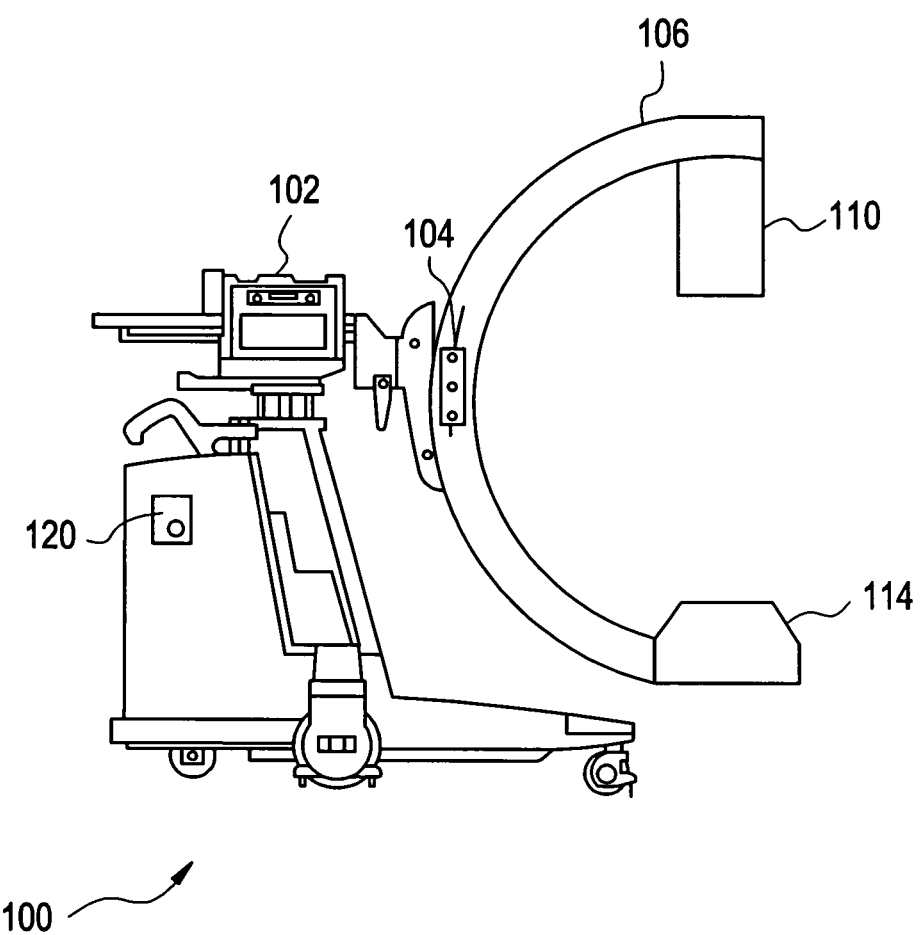
FIG. 6 illustrates an x-ray system according to an embodiment of the present invention.

FIG. 6 illustrates an x-ray system 100 according to an embodiment of the present invention. The x-ray system 100 includes a mobile support structure 102, a bearing assembly 104 and a positioning arm, or C-arm 106. An x-ray detector 110 is connected to one distal end of the C-arm 106, and an x-ray source 114 is connected to another distal end of the C-arm 106. The x-ray system 100 also includes an authorization unit 120 similar to the authorization unit 20 described above.

As mentioned above, embodiments of the present invention may be used with various imaging modalities. For example, the authorization unit may be used with Computed Tomography (CT), X-ray (film-based and digital x-ray systems), Positron Emission Tomography (PET), such as shown and described in U.S. Pat. No. 6,337,481, entitled "Data binning method and apparatus for PET tomography including remote services over a network," which is hereby incorporated by reference in its entirety, Single Photon Emission Computed Tomography (SPECT), such as shown and described in U.S. Pat. No. 6,194,725, entitled "SPECT system with reduced radius detectors," which is hereby incorporated by reference in its entirety, Electron Beam Tomography (EBT), such as shown and described in U.S. Pat. No. 5,442,673, entitled "Fixed septum collimator for electron beam tomography," which is hereby incorporated by reference in its entirety, Magnetic Resonance (MR), and various other imaging systems. Additionally, embodiments of the present invention may also be used with navigation and tracking systems, such as those described in U.S. Pat. No. 5,803,089, entitled "Position Tracking and Imaging System for Use in Medical Applications," which is hereby incorporated by reference in its entirety.

Figure 7:
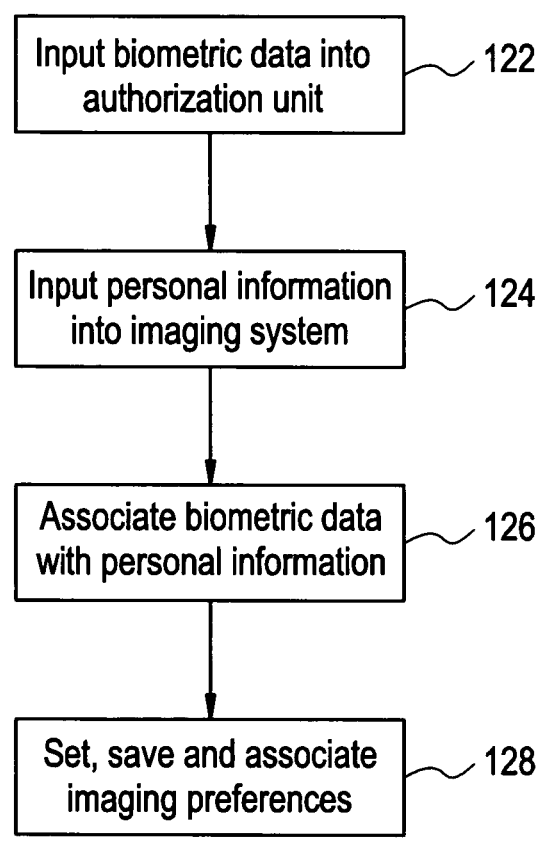
FIG. 7 is a flow chart of a registration process according to an embodiment of the present invention.

FIG. 7 is a flow chart of the registration process according to an embodiment of the present invention. At 122, an individual, such as a physician, technician, or the like, inputs biometric data at an authorization unit. If the individual has previously registered, the imaging system will recognize the individual and he/she may begin using the imaging system. The individual also inputs personal information, including name, at step 124. Optionally, before step 124, the individual may input a password that allows the registration process to continue. At 126, the authorization unit associates the individual's personal information and biometric data with one another. At 128, the individual then has the option to set and save imaging preferences that may be associated with the personal information and biometric data. After registration, the individual may then use the imaging system, and any other imaging system networked thereto. Optionally, the individual may only be authorized to use certain imaging systems within a network. Further, a central management system may keep track of an individual's use of various imaging systems. That is, the central management system may store use data (such as time of use, length of use, results, and the like) in a storage unit. Alternatively, each imaging system within a network may store use data.

The biometric authorization units discussed above may also be used in conjunction with smart cards, and the like to provide additional security against unauthorized use.

Additionally, the biometric authorization units described above may be used with audio/video equipment, such as televisions, VCRs, DVD players, computers, cell phones and the like, to restrict access to those devices to authorized individuals, in an effort to reduce theft of those devices. For example, individuals purchasing audio/video equipment such as televisions, DVD players, CD players, car stereos, etc., may be required to register through a biometric authorization unit, such as authorization unit 20. The audio/video equipment may only be activated through a registered individual inputting a biometric identifier into an authorization unit operatively connected to the audio/video equipment. The individual may then save a password in a data storage unit of the authorization unit that allows additional registrations. Additionally, user preferences may be associated with the biometric data. For example, volume adjustments, station presets, and the like may be associated with the biometric data.

Further, the biometric authorization units discussed above may also be used to restrict access to automated teller machines (ATMs). For example, instead of using a swipe card and a PIN number, a person may access a bank account via an ATM by inputting a biometric identifier into an authorization unit operatively connected to the ATM. A bank may register an individual's biometric data, such as a finger print, with that individual's account. The biometric data of the individual and the account information are then associated with one another. The individual may then access his/her account by inputting a biometric identifier on an authorization unit of an account access station, such as an ATM.

Thus, embodiments of the present invention provide a medical imaging system that provides a higher degree of security. Further, embodiments of the present invention provide an efficient system and method in which only authorized users may use medical imaging systems.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical imaging system comprising:
    a central processing unit;
    a data storage unit in communication with said central processing unit;
    a user control input unit in communication with said central processing unit;
    a display unit in communication with said central processing unit;
    imaging equipment in electrical communication with said central processing unit; and
    a biometric authorization unit in electrical communication with said central processing unit,
    wherein said biometric authorization unit is configured to receive a user input of a biometric identifier,
    wherein at least one of said central processing unit and said biometric authorization unit is configured to:
        extract biometric data from the biometric identifier,
        compare said biometric data with stored biometric data in said data storage unit, and
        enable imaging use of the medical imaging system based on the comparison;
    wherein at least one of said central processing unit and said biometric authorization unit is configured to:
        associate the stored biometric data with stored personal identification information comprising at least one of an operator name, address, and occupation,
        associate user preference information with the associated stored biometric data and stored personal identification information,
        store the associated stored biometric data, stored personal identification information, and user preference information in said data storage unit after an initial registration, and
        automatically adjust imaging equipment acquisition parameters of the imaging equipment based on the user preference information in response to biometric data input at the biometric authorization unit that matches stored biometric data,
    wherein the medical imaging system is one of an ultrasound, Computed Tomography (CT), X-ray, Positron Emission Tomography (PET), Single Photon Emission Computed Tomography (SPECT), Electron Beam Tomography (EBT), Magnetic Resonance (MR), and image-guided surgery system, and
    wherein the biometric identifier is at least one of a fingerprint, handprint, voice, iris, retina, and facial thermogram.

2. The medical imaging system of claim 1, wherein at least one of said central processing unit and said biometric authorization unit is configured to enable imaging use of the medical imaging system when a match exists between the biometric data extracted from the biometric identifier and the stored biometric data.

3. The medical imaging system of claim 1, wherein said central processing unit is configured to store information regarding the use of the medical imaging system in said data storage unit.

4. The medical imaging system of claim 1, wherein said imaging equipment is an ultrasound probe and the medical imaging system is the ultrasound system.

5. The medical imaging system of claim 1, wherein the medical imaging system is configured in a network with at least one other imaging system.

6. A medical imaging network comprising:
    a plurality of medical imaging systems in communication with one another, each of said medical imaging systems comprising:
        a user control input unit;
        a display unit;
        imaging equipment; and
        a biometric authorization unit configured to:
            receive an input of a biometric identifier,
            extract biometric data from the biometric identifier, and
            enable use of the imaging equipment to image a patient based on the biometric identifier input into said biometric authorization unit; and
    a central management station comprising a central processing unit, said central management station in communication with each of said plurality of medical imaging systems,
    wherein said central processing unit stores the biometric data extracted from the biometric identifier in at least one of a central data storage unit in said central management station and individual data storage units in said plurality of imaging systems,
    wherein said central processing unit associates personal identification information comprising at least one of an operator name, address, and occupation and user preference information with the stored biometric data,
    wherein imaging equipment acquisition parameters of the imaging equipment are automatically adjusted based on the user preference information in response to biometric data input at the biometric authorization unit that matches stored biometric data,
    wherein each of the medical imaging systems is one of an ultrasound, Computed Tomography (CT), X-ray, Positron Emission Tomography (PET), Single Photon Emission Computed Tomography (SPECT), Electron Beam Tomography (EBT), Magnetic Resonance (MR), and image-guided surgery system, and
    wherein the biometric identifier is at least one of a fingerprint, handprint, voice, iris, retina, and facial thermogram.

7. The medical imaging network of claim 6, wherein said central processing unit stores use information, including at least one of user identity, time, and length of an imaging session at each of said plurality of imaging systems, within at least one of said central management station and any of said plurality of imaging systems.

8. The medical imaging network of claim 6, wherein one of:
    said central management station, and
    one of said plurality of imaging systems, register a user.

9. The medical imaging network of claim 6, wherein at least one of said plurality of medical imaging systems is said ultrasound system and said imaging equipment of said at least one of said plurality of medical imaging systems is an ultrasound probe.

10. A method of using a medical imaging system comprising a user control input unit, a display unit, and imaging equipment, the method comprising:
- registering to use the medical imaging system, said registering comprising:
  - (i) inputting a biometric identifier into a biometric authorization unit;
  - (ii) inputting personal information into the medical imaging system, the personal information comprising at least one of an operator name, address, and occupation; and
  - (iii) associating biometric data extracted from the biometric identifier with the personal information;
- storing the biometric data and associated personal information;
- storing user preference information and associating the user preference information with the associated stored biometric data and personal information; and
- enabling imaging use of the medical imaging system and automatically adjusting imaging equipment acquisition parameters of the imaging equipment based on the user preference information in response to biometric data input at the biometric authorization unit that matches stored biometric data,
- wherein the medical imaging system is one of an ultrasound, Computed Tomography (CT), X-ray, Positron Emission Tomography (PET), Single Photon Emission Computed Tomography (SPECT), Electron Beam Tomography (EBT), Magnetic Resonance (MR), and image-guided surgery system, and
- wherein the biometric identifier is at least one of a fingerprint, handprint, voice, iris, retina, and facial thermogram.

11. The method of claim 10, further comprising allowing said registering step by inputting a password.

* * * * *